United States Patent
Indovina et al.

(10) Patent No.: US 9,629,529 B1
(45) Date of Patent: Apr. 25, 2017

(54) SPECULUM WITH COLOR FILTER

(71) Applicant: THI Medical, LLC, Chandler, AZ (US)

(72) Inventors: Anthony V. Indovina, Phoenix, AZ (US); Gerald T. Harder, Chandler, AZ (US)

(73) Assignee: THI Medical, LLC, Chandler, AZ (US)

( * ) Notice: Subject to any disclaimer, the term of this patent is extended or adjusted under 35 U.S.C. 154(b) by 0 days.

(21) Appl. No.: 15/294,504

(22) Filed: Oct. 14, 2016

Related U.S. Application Data

(60) Provisional application No. 62/242,764, filed on Oct. 16, 2015.

(51) Int. Cl.
  *A61B 1/06* (2006.01)
  *A61B 1/32* (2006.01)
  *A61B 1/303* (2006.01)

(52) U.S. Cl.
  CPC ............ *A61B 1/0646* (2013.01); *A61B 1/303* (2013.01); *A61B 1/32* (2013.01)

(58) Field of Classification Search
  CPC ......... A61B 1/0646; A61B 1/32; A61B 1/303; A61B 17/3421
  See application file for complete search history.

(56) References Cited

U.S. PATENT DOCUMENTS

| | | | |
|---|---|---|---|
| 3,985,125 A | 10/1976 | Rose | |
| 4,043,646 A * | 8/1977 | Heine | A61B 1/0669 351/213 |
| 4,206,750 A | 6/1980 | Kaivola | |
| 4,432,351 A | 2/1984 | Hoary | |
| 4,597,383 A | 7/1986 | VanDerBel | |
| 4,766,887 A | 8/1988 | Cecil, Jr. et al. | |
| 4,959,710 A * | 9/1990 | Uehara | A61B 1/0638 348/E5.038 |
| 4,971,036 A | 11/1990 | Collins | |
| 4,994,070 A | 2/1991 | Waters | |
| 5,231,973 A | 8/1993 | Dickie | |
| 5,392,764 A | 2/1995 | Swanson et al. | |
| 5,465,709 A | 11/1995 | Dickie et al. | |
| 5,499,964 A | 3/1996 | Beck et al. | |
| 6,004,265 A | 12/1999 | Hsu et al. | |
| 6,036,638 A | 3/2000 | Nwawka | |
| 6,719,687 B1 | 4/2004 | Van Der Weegen | |
| 7,029,438 B2 | 4/2006 | Morin et al. | |
| 7,311,663 B2 | 12/2007 | Marcotte | |
| 7,668,450 B2 | 2/2010 | Todd et al. | |

(Continued)

*Primary Examiner* — Andrew Yang
(74) *Attorney, Agent, or Firm* — Cahill Glazer PLC

(57) ABSTRACT

A speculum includes a body portion of generally cylindrical shape having a distal end for insertion into a body cavity, and a proximal end from which internal body tissues may be examined. A handle extends laterally from the proximal end of the speculum body. A light source providing broad spectrum white light may be supported within the handle. A light channel extends along and through the speculum body to direct light from the light source in the handle toward the distal end of the speculum body in order to illuminate the body cavity. One or more color filters are selectively disposed between the light source and the light channel to selectively illuminate the body cavity with light of a corresponding color spectrum.

24 Claims, 11 Drawing Sheets

(56) References Cited

U.S. PATENT DOCUMENTS

| | | |
|---|---|---|
| 7,758,203 B2 | 7/2010 | McMahon et al. |
| 8,118,738 B2 | 2/2012 | Larkin |
| 8,142,352 B2 | 3/2012 | Vivenzio et al. |
| 8,157,728 B2 | 4/2012 | Danna et al. |
| 8,376,942 B2 | 2/2013 | Krauter et al. |
| 8,388,523 B2 | 3/2013 | Vivenzio et al. |
| 8,435,175 B2 | 5/2013 | McMahon et al. |
| 2008/0228038 A1 | 9/2008 | McMahon et al. |
| 2008/0269565 A1 | 10/2008 | McMahon et al. |
| 2008/0319269 A1 | 12/2008 | Longo et al. |
| 2010/0305406 A1* | 12/2010 | Braun .................. H01C 7/006 600/202 |

* cited by examiner

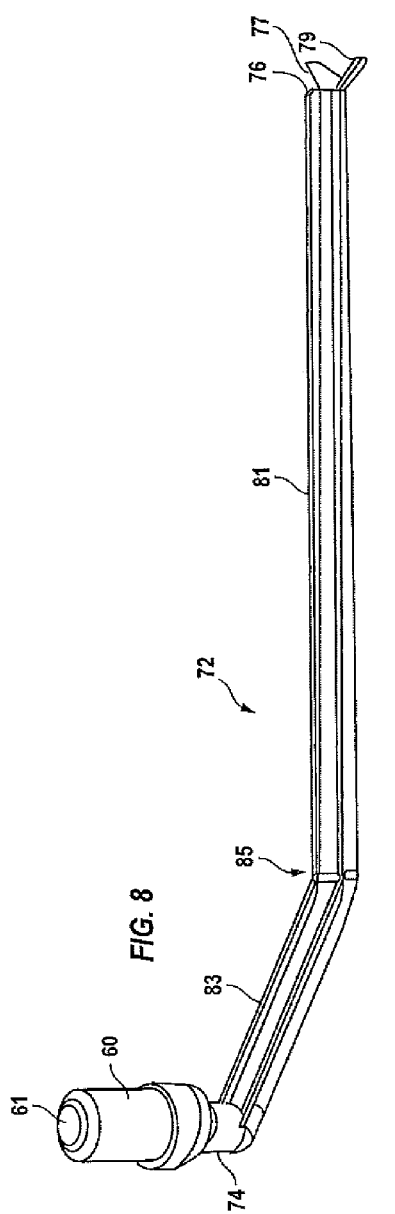
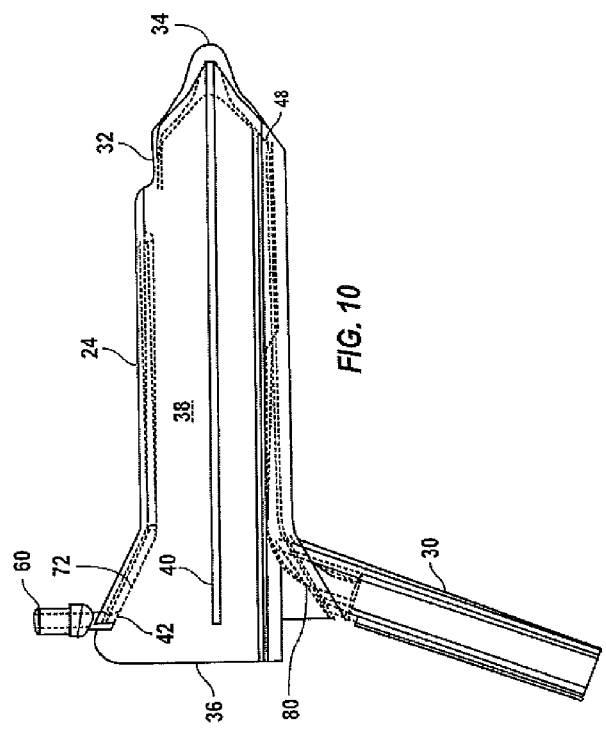
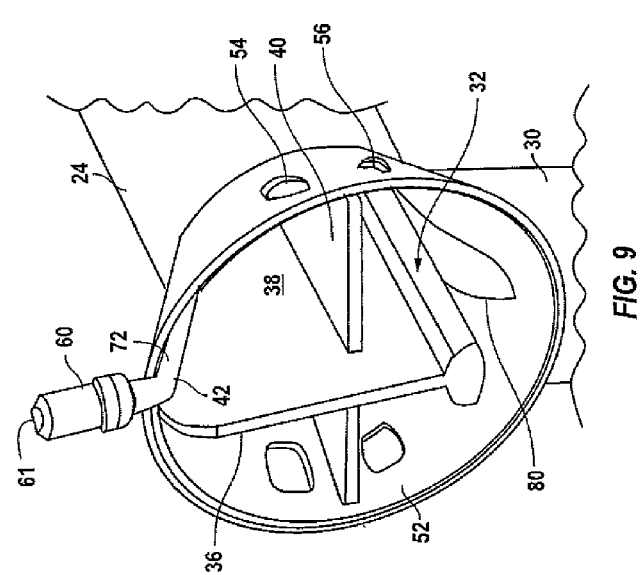
FIG. 8
FIG. 10
FIG. 9

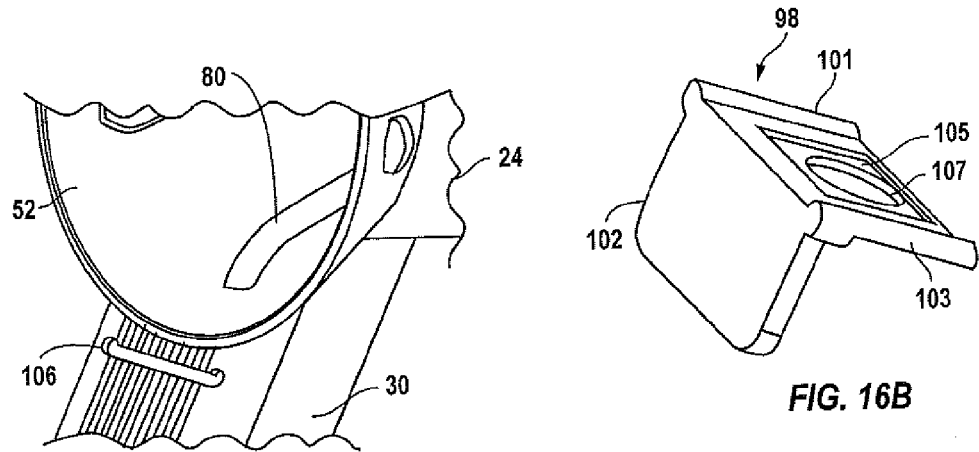
FIG. 16A
FIG. 16B
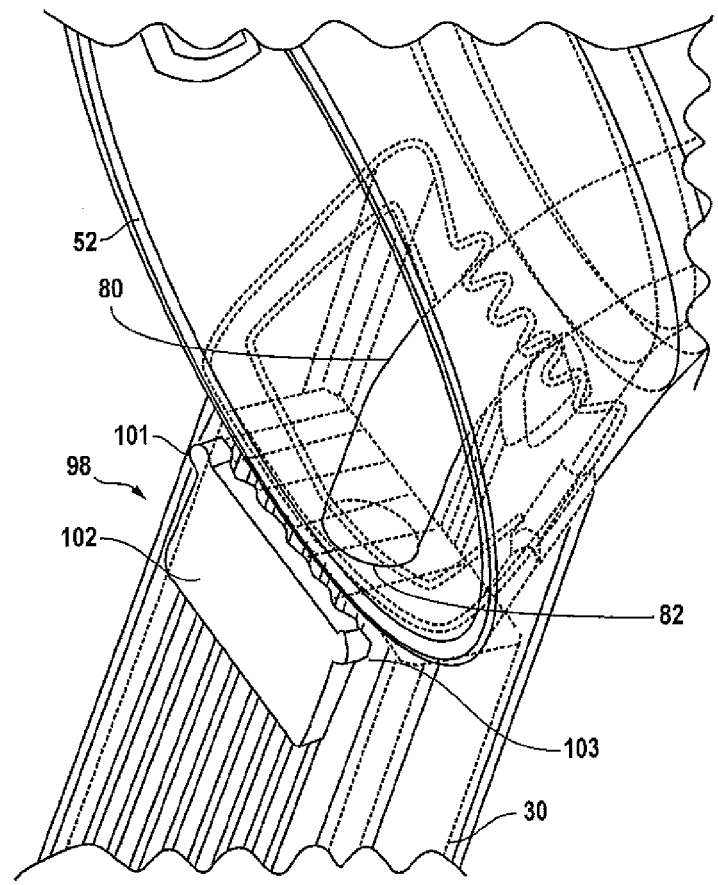
FIG. 17

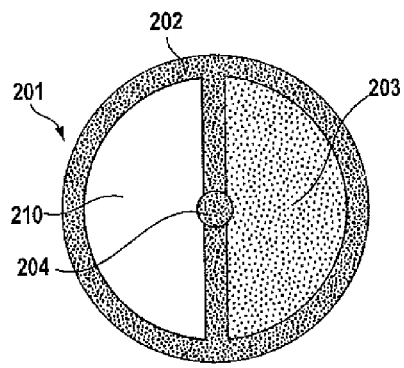
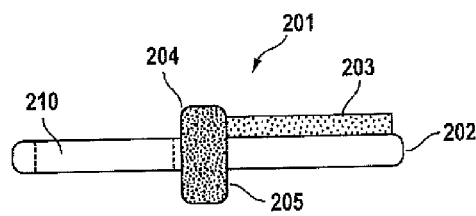
FIG. 18
FIG. 19
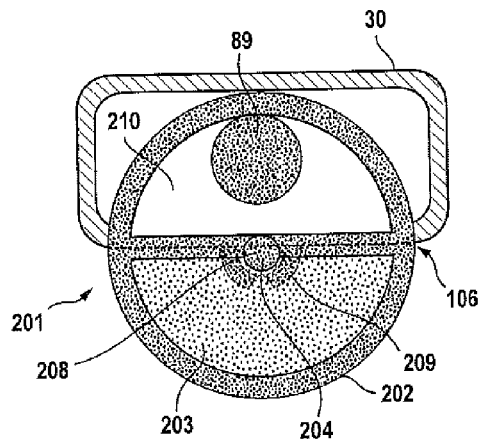
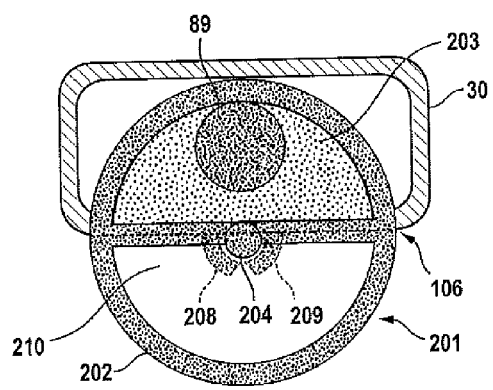
FIG. 20
FIG. 21
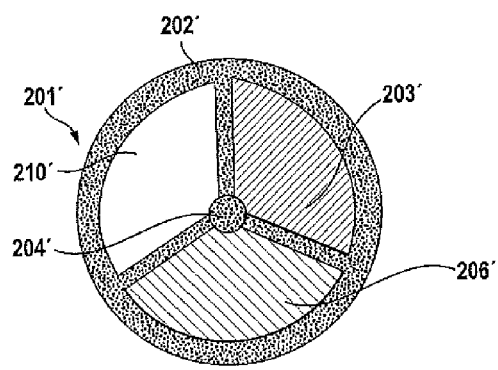
FIG. 29

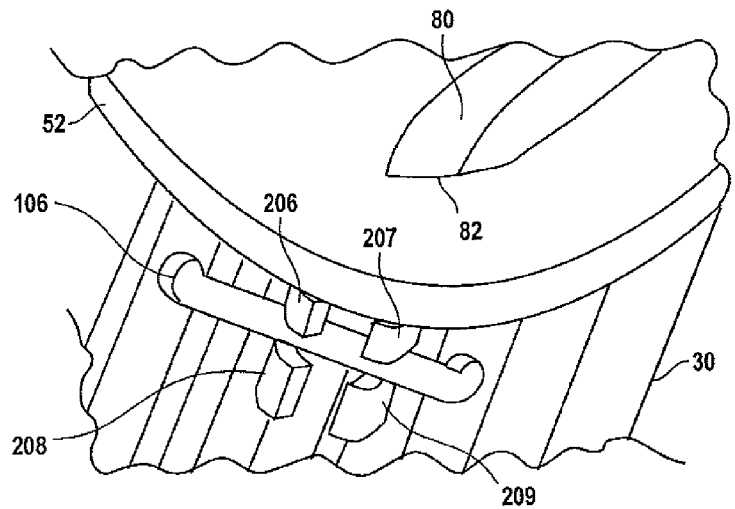
FIG. 22
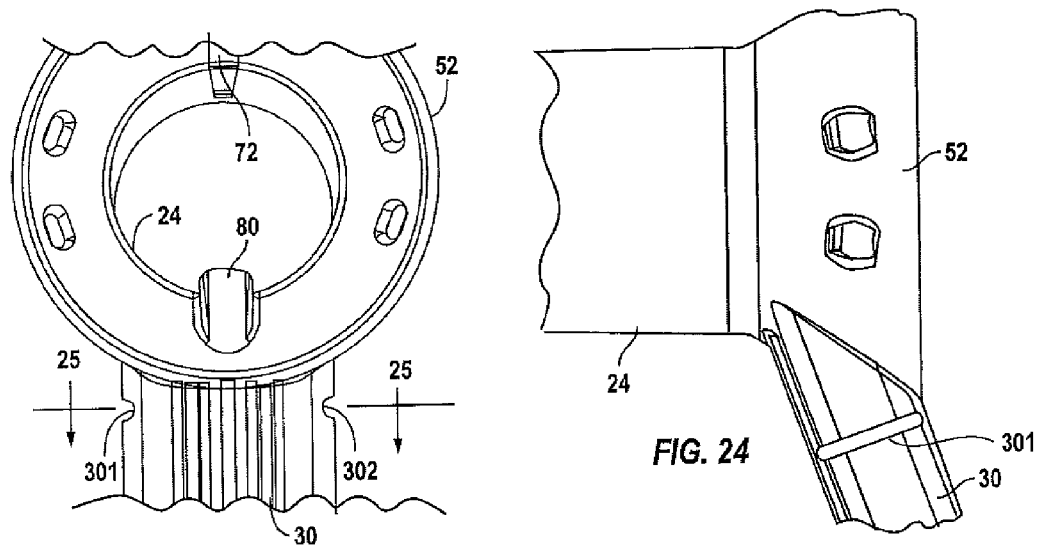
FIG. 23
FIG. 24
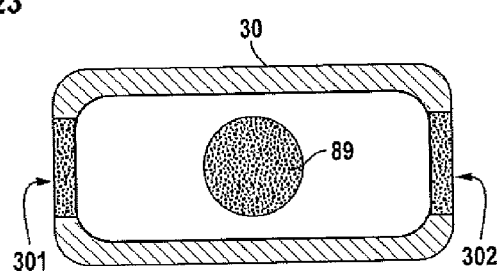
FIG. 25

SPECULUM WITH COLOR FILTER

CROSS-REFERENCE TO RELATED PATENT APPLICATIONS

This non-provisional patent application claims the benefit of prior-filed U.S. provisional patent application No. 62/242,764, filed on Oct. 16, 2015, under 35 U.S.C. 119(e).

BACKGROUND OF THE INVENTION

1. Field of the Invention

The present invention relates generally to the field of medically examining and surgically operating upon orifices of the human body, including gynecological examination and surgery, and more particularly, to a speculum for such purposes.

2. Description of the Related Art

Gynecologists often employ speculum devices for the purpose of examining and operating upon the lower genital tract. The standard speculum which is commonly used is a duck-billed design that can be inserted into the vaginal orifice and then opened to permit visualization of the upper vagina and cervix uteri. One example of such a duck-billed speculum is disclosed in U.S. Pat. No. 4,206,750 issued to Kaivola. Another example of such a duck-billed speculum is disclosed in U.S. Pat. No. 8,157,728 issued to Danna, et al.

The standard duck-billed speculum has two pieces that are pivotally connected by a hinge to allow opening and closing to various aperture sizes. The upper duck-bill piece faces downward and attaches to a similarly-shaped lower duck-bill with a mechanical hinge. The tips of the two duck-bills can be spread apart from each other by holding the base of the lower duck-bill and applying pressure with the thumb on the downwardly-extending handle of the upper duck-bill piece. The line of sight extending just below the upper duck-bill portion of the speculum provides visualization of the vaginal and cervical surfaces for examination. In some cases, the duck-bills can be locked into a fixed position at a desired opening size for hands-free use during examination or surgical procedures.

During some surgical procedures performed by gynecologists, it is necessary to excise abnormal, pre-cancerous tissue and cauterize tissue margins for hemostasis. Cauterization involves the application of heat to tissues of the body to reduce bleeding and safely effect the removal of abnormal tissue. Gynecologists may perform cauterization by inserting a metal probe or loop through the speculum, and heating the tip of the metal probe or loop with electric current to burn tissue contacted by the heated probe or loop. The burning of such tissue is always accompanied by the production of smoke and/or toxic vapors.

It is known to provide a surgical speculum with a smoke evacuator tube for connection to a vacuum apparatus in order to suction away vapors produced during surgical procedures. The Occupational Safety and Health Act requires that such offensive vapors, or effluvium, be evacuated, since these gasses can be toxic. Furthermore, the smoke generated when tissue is cauterized can obstruct proper visualization during surgical excision procedures, and must therefore be evacuated to allow the surgeon to see what he or she is doing. One example of a gynecological speculum that includes a smoke removal tube is shown in U.S. Pat. No. 5,392,764 to Swanson, et al.

During use, a conventional duck-billed speculum is inserted into the vaginal opening with the upper and lower duck-bills in their closed (i.e., smallest diameter) position, lying adjacent to each other. Once inserted, the operator uses thumb pressure to separate the distal ends of the upper and lower duck-bills, which opens the aperture of the speculum. Once the speculum is opened, the vaginal cavity and cervix are exposed for examination and/or performing surgical procedures.

While conventional duck-billed specula, as described above, are satisfactory for some purposes, they also present several disadvantages, especially when surgical procedures are necessary on the cervix, e.g., Loop Electrosurgical Excision Procedure (LEEP). The moving parts of the mechanically hinged speculum can pinch tissue, causing pain leading to abrupt movement by the patient, and increased danger during surgical procedures. As the operator advances the closed duck-bill speculum into the vaginal opening, the patient's skin tissue is exposed to the gap between the two duck bills. Furthermore, with full deployment of the duck-billed speculum, the lateral vaginal walls protrude between the separated duck-bills of the speculum and are exposed to electrical current or laser energy which can cause patient injury even at the hands of the most skilled operator. Accidental injury to the patient is especially likely when vaginal tissue is pinched during the examination. The resulting patient discomfort can produce a "startle reaction", which can lead to abrupt inadvertent movement by the patient, which is especially dangerous when electric or laser energy is being utilized during a procedure.

Another disadvantage of the conventional duck-billed speculum is that proper visualization of the cervix and upper vagina sometimes cannot be achieved due to collapsing of the vaginal walls, especially in multiparous patients (those who have had one or more vaginal births). In order to maximize the diagnostic value of any examination, the entire vaginal and cervical epithelium must be well-visualized. However, the aperture provided by the opened duck-bill speculum is relatively small.

When using a speculum for gynecological purposes, the field to be viewed must be illuminated during examination and/or surgical procedures. Lighting for such an examination is provided by an external source, of which several options are available. For example, a free-standing gooseneck lamp may be placed over the shoulder of the physician. Alternatively, an electric head-lamp may be affixed to the physician's forehead by an elastic band in such a manner that the beam of light is directed into the speculum as the physician looks into the speculum. Another option is to provide a portable light source, such as described by McMahon, et al., in U.S. Pat. No. 7,758,203 and assigned to Welch Allyn, Inc.; in the embodiment specifically disclosed therein, a rechargeable light source is removably inserted within a handle of a disposable, examination-only type speculum, and an optical light pipe guides light emitted by the rechargeable light source along the lower duck-bill member of the speculum toward the field to be examined. For specialized examinations, a vaginal microscope, or colposcope, is utilized. A conventional colposcope is equipped with its own light-source, and usually provides different colors along the light frequency spectrum to better distinguish particular features of the vaginal and cervical epithelium.

Notwithstanding the efforts of others to incorporate light sources within a gynecological speculum, lighting currently provided for surgical procedures of the upper vagina and cervix is often insufficient since known duck-bill specula available for surgical use rely on external light sources which do not illuminate the cervix with uniformity. Also, if specialized light of a particular color is needed, an expensive colposcope apparatus is necessary. Manufacturers of colposcopes have provided color filters in the past to provide a light of a particular color; specifically a blue-green. The blue-green light provides optimal color contrast with blood vessels, thus making them appear darker and more easily visible. However, colposcopes are significantly more expensive than a simple speculum. Due to their significant expense, such colposcopes are often unavailable to medical practitioners in undeveloped areas of the world, where cervical cancer is a major cause of death for the female population. Moreover, even when a colposcope is available, it cannot be used by itself to gain access within orifices to the body; some other tool, e.g., a speculum, must still be used to open the orifice sufficiently to gain physical and visual access thereto.

While light sources have been incorporated into the handle of disposable duck-billed specula used for examination purposes only, those specula do not lend themselves to use for performing gynecological surgical procedures. There are no specula known to the applicants adapted to performing gynecological surgical procedures that incorporate a light source.

Apart from variable-diameter duck-billed specula described above, fixed-diameter cylindrical specula have also been described for the purpose of examination of the vagina and cervix. For example, within U.S. Pat. No. 5,392,764 to Swanson, et al., referenced above, a generally-cylindrical speculum is disclosed which is somewhat tapered along its length to have a fixed-diameter distal end and a slightly-larger fixed diameter at its proximal end. As already mentioned, the disclosed device includes a smoke removal tube. However, the design disclosed in the '764 Swanson patent suffers from several disadvantages. First, the smoke evacuation tube, and its vacuum port, impinge upon the physician's line of sight along the speculum, and obscure proper visualization of the upper vagina and cervix. Second, the design disclosed in the '764 Swanson patent does not incorporate a lighting source within the speculum itself; accordingly, a physician using such speculum must rely upon an external light source, which does not allow full illumination of the operative field. Third, insertion of the Swanson speculum may cause discomfort to the patient during insertion. Unlike the duck-billed speculum which has a somewhat closed profile at its distal end during insertion, the Swanson speculum presents an open distal face, with exposed edges along its full diameter at its distal end. Finally, the speculum disclosed in the Swanson '764 patent relies on an angled opening at the distal end to allow access to the cervix; this angle may not allow for the cervix to present itself within the distal opening in all patients.

It is known in the art of medical devices to produce light of a desired color by selectively activating inexpensive light sources (e.g., light emitting diodes) of the primary colors (i.e., red, green and blue). By controlling the intensity, pulse width, and/or duty cycle of the three primary light sources, a resulting light can be generated which, at least to the human eye, appears to be a color of a particular desired frequency. In practice, however, a portable light using red, green, and blue light emitting diodes to produce light of a specific color requires a sophisticated electronic design, and thus requires a customized solution for the application.

Thus, a need remains for a simple speculum for use during both examining and operative procedures which overcomes the limitations of specula that are already known.

It is therefore an object of the present invention to provide a speculum that may be used to perform gynecological procedures, as well as examining and surgical procedures within other orifices of the body, which can be inserted and employed with minimal patient discomfort.

Another object of the present invention is to provide such a speculum which is lightweight and easily retained at a desired position within the vagina, or other body opening, for hands-free use by a physician, particularly during surgical procedures.

Yet another object of the present invention is to provide such a speculum that enables a physician to more completely visualize the cervix or other body orifice, and to perform operative procedures upon a relatively large area of the upper vagina, cervix, or other body orifice.

A further object of the present invention is to provide such a speculum that can illuminate the tissues within a body orifice with light from two or more different portions of the visible color spectrum.

A yet further object of the present invention is to provide such a speculum that allows a physician to quickly and easily change the color spectrum of the light being used to illuminate the tissues within a body orifice.

Still another object of the present invention is to provide such a speculum that incorporates a smoke evacuation apparatus to remove smoke that would otherwise interfere with visualization of the tissues to be viewed and surgically operated upon.

A further object of the present invention is to provide such a speculum adapted to permit surgical procedures to be performed upon exposed tissues, while providing sufficient illumination for a physician to clearly visualize, examine, and surgically operate upon, the genital epithelium or other tissues of interest.

A still further object of the present invention is to provide such a speculum adapted to permit surgical procedures to be performed upon exposed tissues, while providing maximum safety, decreased risk of injury, and increased comfort to the patient.

Yet another object of the present invention is to provide such a speculum that can be manufactured inexpensively from molded plastic components.

A further object of the invention is to provide such a speculum that is so inexpensive as to be adapted to one-time use, thereby avoiding the need for sterilization and minimizing risk of infection to patients.

Still another object of the present invention is to provide such a speculum capable of being used as an anal speculum.

These and other objects of the present invention will become more apparent to those skilled in the art as the description thereof proceeds.

SUMMARY OF THE INVENTION

Briefly described, and in accordance a first preferred embodiment thereof, the present invention is a speculum used to examine tissues within an orifice of the body. The speculum has a generally cylindrical body having a generally cylindrical hollow passageway extending therethrough. The cylindrical body of the speculum includes an open distal end for insertion into a vaginal area, or other body opening, and an opposing open proximal end through which the tissues exposed by the open distal end may be examined. A handle is preferably coupled to the proximal end of the generally cylindrical speculum body. The handle extends generally laterally from the proximal end of the generally cylindrical body.

A light source is housed within the handle and provides light used to illuminate the tissues being examined. In the preferred embodiment, the light source is battery-operated and includes a rechargeable battery. A light channel, or light guide, extends along the generally cylindrical body of the speculum between a first end located proximate to the handle, and an opposing second end located generally proximate to the distal end of the speculum body. The first end of the light channel receives light emitted by light source. The light channel directs light received at its first end to its second end for emitting the received light toward the tissues being examined.

At least one color filter is selectively insertable within a space disposed between the light source and the first end of the light channel for determining the color of the light that illuminates the tissue under examination. Preferably, the at least one color filter is also selectively removable from the space disposed between the light source and the first end of the light channel; in one embodiment of the present invention, removal of the at least one color filter allows unfiltered broad spectrum white light to pass directly from the light source to the first end of the light channel for illumination of the tissue being observed.

In one preferred embodiment of the invention, the handle of the vaginal speculum includes a slot into which a removable color filter may be inserted; when so-inserted, the color filter is located directly between the output of the light source and the first end of the light channel that is incorporated into the speculum body. In this case, the light received by the first end of the light channel is determined by the color of the inserted filter. Alternatively, if the color filter is removed, then broad spectrum white light provided by the light source is directed into the first end of the light channel. Two or more different color filter inserts may be provided, if desired, to switch between different light spectrums. In a preferred embodiment, a slot is provided in the handle of the speculum, and the color filter insert is removably inserted into the handle through such slot.

In another preferred embodiment, at least one color filter is incorporated into a movable filter assembly incorporated within the handle. A selector element is coupled to the movable filter assembly and is accessible by the user via the exterior of the handle for allowing the user to move the filter assembly between at least a first position in which a color filter is located between the light source of the first end of the light channel, and a second position in which such color filter is not located between the light source and the first end of the light channel.

If desired, the above-described movable filter assembly may be provided as a rotatable color wheel, which can be rotatably supported within the speculum handle and rotated by the user. Rotation of the filter wheel can position a color filter directly between the light source and the light guide for selecting the color of the light used to illuminate the tissues under examination. Further rotation of the filter wheel to a different position can either select another filter of a different color, or no filter at all; in the latter case, direct, unfiltered broad spectrum white light is guided to the area under examination.

In yet another preferred embodiment, one or more color filters may be placed on an elongated filter assembly that is slidingly supported by the speculum handle. The user can slide the assembly to place a color filter directly between the light source and the light guide, thereby selecting the color of the light that illuminates the tissue under examination. The user may thereafter slide the elongated filter assembly to a different position, either to select a different color filter or no filter at all; again, in the latter case, the light source would then provide direct, unfiltered, broad-spectrum white light to the area under examination.

The color filters described above are preferably relatively thin, for example, having a thickness in the range of 0.003 to 0.005 inch. In the preferred embodiment, at least one such color filter passes light that is within the blue-green spectrum of light.

If desired, a removable obturator may also be provided to assist with initial insertion of the speculum. The obturator has a generally cylindrical body adapted to slidingly extend within the generally cylindrical hollow passageway of the speculum body. The distal end of the obturator is closed upon itself to form a generally rounded dome. The outer diameter of the obturator approximates the inner diameter of the speculum body, allowing the obturator to be slidingly inserted into the hollow passageway of the speculum body through the proximal end thereof. When the obturator is inserted into the speculum, the distal end of the obturator extends beyond the distal end of the speculum, closing the normally open distal end of the speculum. The obturator is removably inserted into the speculum body, with the rounded distal end of the obturator extending beyond the distal end of the generally cylindrical speculum body, thereby easing insertion of the speculum body into the vaginal area or other body opening. The obturator is thereafter removed once the speculum is placed within the vaginal area or other body opening.

Also if desired, the speculum body may include a smoke evacuation channel and vacuum port for removing any smoke and/or noxious gases produced during cauterization of tissues, or other surgical procedures.

BRIEF DESCRIPTION OF THE DRAWINGS

FIG. 8 is a perspective view of the smoke evacuation insert that forms part of the smoke evacuation channel.

FIG. 9 is as perspective view of the upper-rear portion of the speculum body after the insert of FIG. 8 is assembled thereto, and illustrating how the obturator abuts the smoke evacuation insert.

FIG. 10 is a cutaway side view showing the obturator inserted into the speculum body.

FIG. 16A is a partial perspective view of the proximal end of the speculum body and showing a slot for receiving a color filter inserted between the light source and the light pipe in accordance with a preferred embodiment of the present invention.

FIG. 16B is a perspective view of a color filter insert adapted to be slidingly received within the slot shown in FIG. 16A.

FIG. 17 is a partial perspective view showing the color filter insert of FIG. 16B after being inserted within the slot of the speculum shown in FIG. 16A.

FIG. 18 is a top view of a circular color filter assembly, in accordance with an alternate preferred embodiment of the present invention.

FIG. 19 is a side view of the circular color filter assembly shown in FIG. 18.

FIG. 20 is a cross-sectional view of the handle portion of the speculum with the color filter assembly of FIGS. 18 and 19 inserted therein, and allowing unfiltered light to pass directly therethrough.

FIG. 21 is the same cross-sectional view shown in FIG. 20, but after the circular color filter assembly has been rotated 180-degrees to impose the color filter within the light path.

FIG. 22 is a close-up perspective view of the speculum handle, and including flexible retaining fingers used to releasably grasp the pivot post of the circular color filter assembly, in accordance with an alternate preferred embodiment of the present invention.

FIG. 23 is a partial rear view of the speculum in accordance with an alternate preferred embodiment of the present invention, wherein slots are formed in the opposing sides of the handle to slidingly-receive elongated color filter inserts.

FIG. 24 is a side view of the speculum shown in FIG. 23.

FIG. 25 is a top sectional view of the speculum handle shown in FIG. 23 taken through the plane indicated by lines 25-25 within FIG. 23.

FIG. 29 is a top view of an alternate circular color filter assembly wherein two different color filters are included, along with a transparent region for passing unfiltered light.

DETAILED DESCRIPTION OF THE PREFERRED EMBODIMENTS

Figure 1:
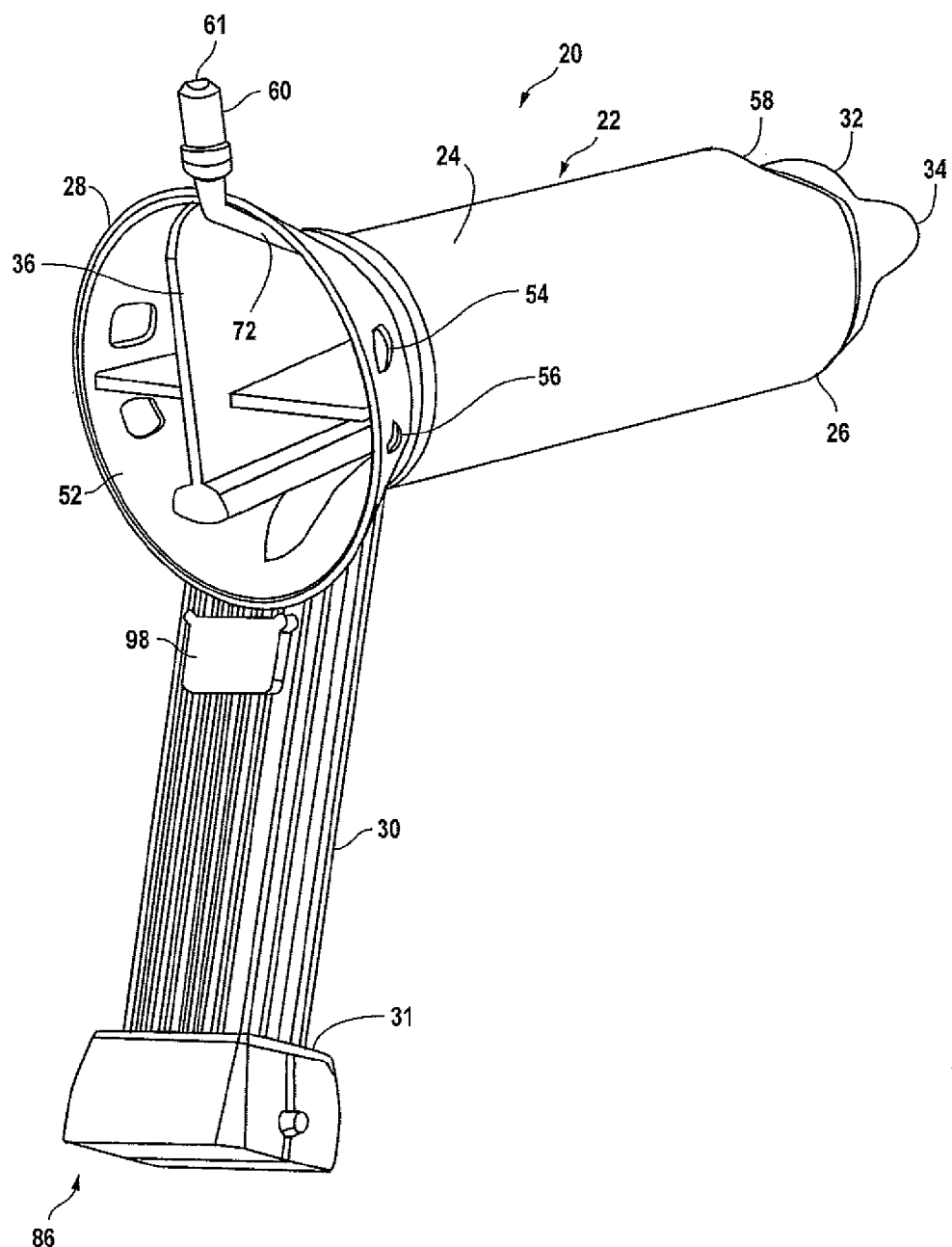
FIG. 1 is a perspective view of a vaginal speculum, including a smoke evacuation insert, color filter, and associated obturator in accordance with a preferred embodiment of the present invention.

A speculum assembly constructed in accordance with a preferred embodiment of the present invention is designated generally within FIG. 1 by reference numeral 20. For purposes of the present description, it is assumed that assembly 20 is used to perform gynecological procedures; however, the specula described herein may also be used as anal specula with only minor modifications, if any at all. Assembly 20 includes a gynecologic speculum, also known as a vaginal speculum, 22. Speculum 22 includes a generally cylindrical speculum body 24 having a distal end 26 for insertion into a vaginal area, and an opposing proximal end 28. A handle 30 is coupled to proximal end 28 of speculum body 24, and extends generally laterally therefrom.

Still referring to FIG. 1, assembly 20 may also include an obturator 32 extending between a distal closed end 34 and an opposing proximal end 36. Obturator 32 is removably inserted within a hollow, generally cylindrical passageway extending through speculum body 24 in a manner to be described in greater detail below. Obturator 32 is inserted within speculum body 24 before placing the speculum 22 within a patient's vagina. As shown in FIG. 1, the rounded distal end 34 of obturator 32 extends beyond distal end 26 of speculum body 24. As can also be seen in FIG. 1, distal end 34 of obturator 32 has a tapered, dome-shaped tip, closed upon itself, to ease insertion of speculum 22 into the vaginal region of the patient. Once speculum 22 has been placed, obturator 32 is removed from speculum body 24 to permit the physician to visualize and/or operate upon an area of interest.

Still referring to FIG. 1, assembly 20 also includes a color filter assembly 98 which is inserted into the handle 30 of speculum body 24 through a slot in handle 30. A light source 86 is also inserted into handle 30 of speculum body 24 through an opening in the lower portion 31 of handle 30. The output of light source 86 is located at the top end, and shines through color filter assembly 98 before entering speculum body 24.

Figure 2:
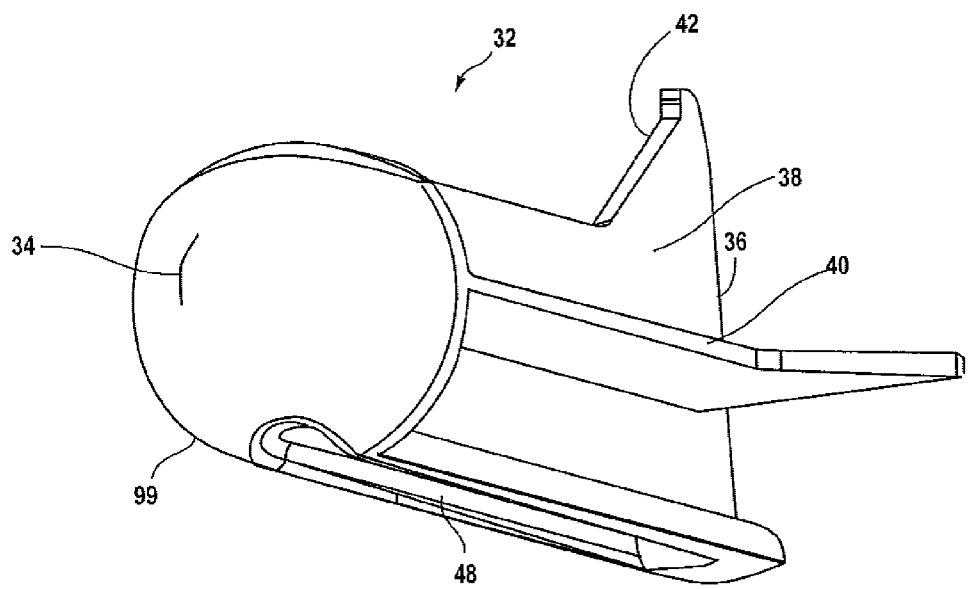
FIG. 2 is a perspective view of the obturator shown in FIG. 1 as viewed from the front end of the obturator.
Figure 3:
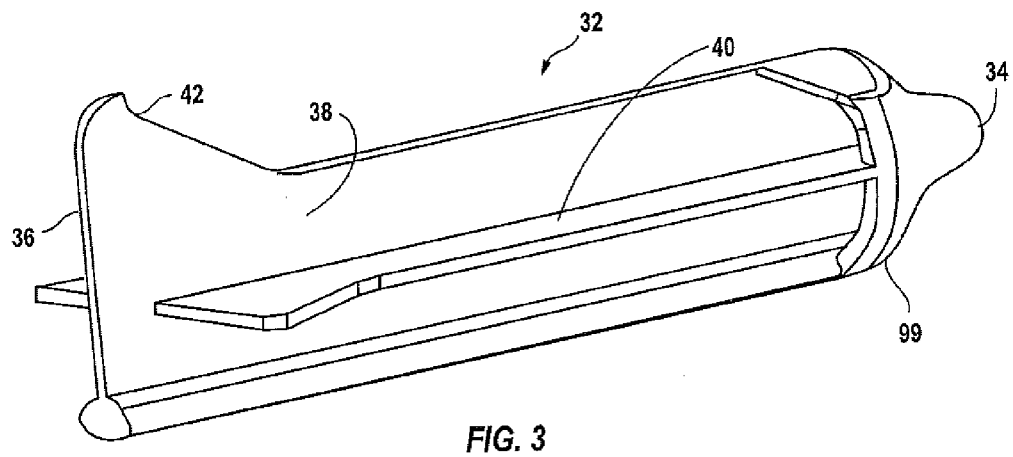
FIG. 3 is a perspective view of the obturator shown in FIGS. 1 and 2 as viewed from the side, and slightly behind, the obturator.

Obturator 32 is shown in greater detail in FIGS. 2 and 3. Portion 99 of distal end 34 is generally cylindrical and is of approximately the same diameter as the inner diameter of the generally cylindrical passageway extending through speculum body 24. In this manner, the generally cylindrical surface 99 of obturator 32 slidingly engages the hollow passageway of speculum body 24. While cylindrical portion 99 of obturator 32 could fully extend to proximal end 36, if desired, this is not required. As shown in FIGS. 2 and 3, the proximal end 36 of obturator 32 may simply include an elongated planar member 38 reinforced by a laterally-extending fin 40. As shown in FIGS. 2 and 3, proximal end 36 of obturator 32 preferably includes an upper projecting tab 42. A lower projecting tab may also be provided, if desired.

As shown best in FIG. 2, the bottom portion of obturator 32 includes an elongated recess 48. As will be explained in greater detail below, recess 48 permits obturator 32 to slide past a lower light guide channel.

Figure 4:
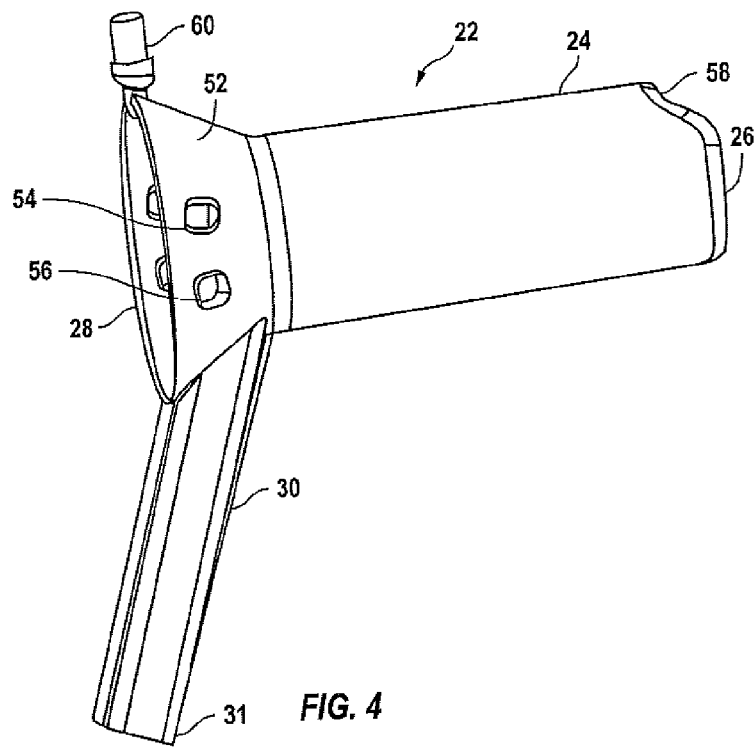
FIG. 4 is a side view of the speculum body including the smoke evacuation insert, with the obturator removed.
Figure 5:
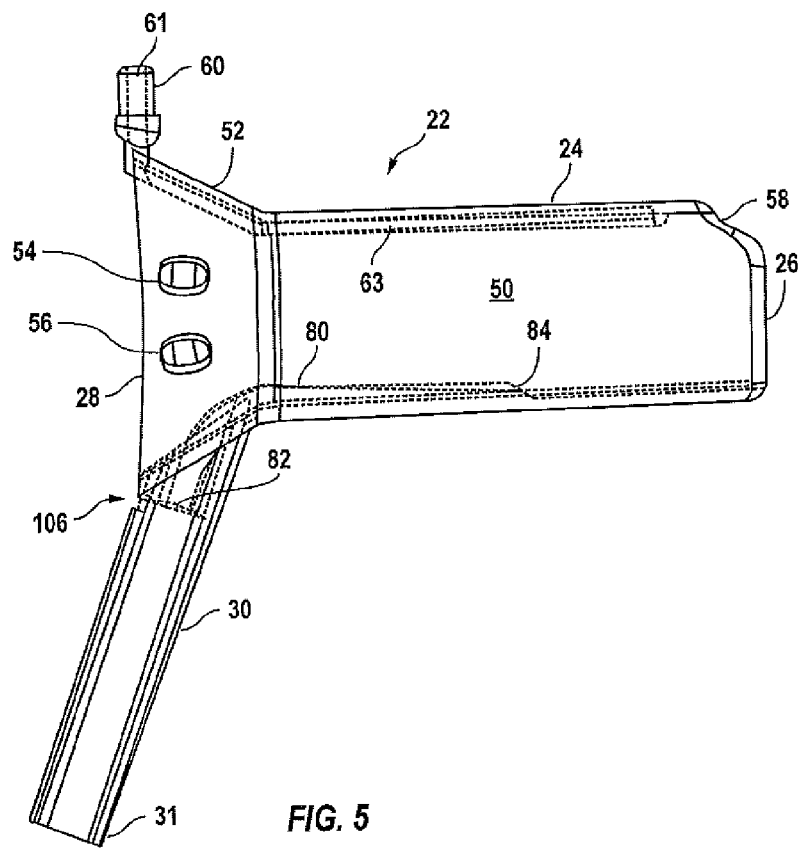
FIG. 5 is a cross-sectional view of the speculum body including the smoke evacuation insert, shown in FIG. 4.

Turning to FIGS. 4 and 5, speculum 22 includes speculum body 24 formed by a generally cylindrical tube extending from distal end 26 to proximal end 28. Speculum body encloses a generally cylindrical hollow passageway 50 extending from the open proximal end 28 through the open distal end 26. Proximal end 28 preferably tapers outwardly to form a truncated cone 52. A series of apertures, or "fenestrations" 54 and 56, preferably of generally oval shape, are formed within truncated cone 52 about its periphery to allow a physician to pass sutures therethrough. In this manner, the physician can suture truncated conical portion 52 of speculum body 24 to the patient's body; once sutured in place, the physician need not grasp the handle of the speculum body in order to maintain it at the selected location, and the physician can thereafter use both of his or her hands to attend to surgical procedures.

Handle portion 30 is coupled to proximal end 28 of speculum body 24 and extends generally laterally therefrom. Handle 30 serves three primary functions. First, the physician grasps handle 30 during initial placement of speculum 22; obturator 32 is present during such initial placement, and the physician may conveniently grasp handle 30 with the fingers of one hand while using the thumb of the same hand to engage proximal end 36 (see FIG. 1) of obturator 32 while guiding the assembly 20 into the vaginal region. Second, after removing obturator 32, the physician can use handle 30 to direct, or "steer", distal end 26 of speculum 22 toward the area to be examined and/or operated upon; in this regard, the physician looks through conical portion 52 of proximal end 28, and through central passageway 50, and can easily visualize tissues located at the open distal end 26. Third, handle 30 is used to receive a removable light source 86, described in greater detail below, to illuminate the area being examined and/or surgically operated upon.

Figure 11:
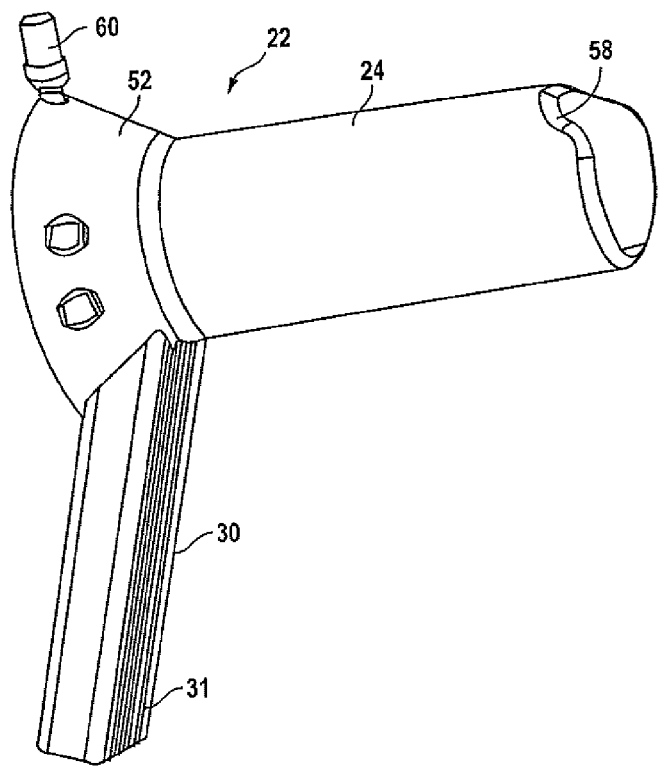
FIG. 11 is a perspective view of the speculum body including the smoke evacuation insert showing the formation of a notched opening formed in the front/distal end thereof.

The open distal end 26 of speculum body 24 preferably includes a recessed, or notched, portion 58. As shown in FIGS. 4, 5 and 11, notch 58 is preferably aligned with the top of speculum body 24. Notch 58 allows a portion of a patient's cervix to enter into the field of view of hollow passageway 50 of speculum body 24 for the vast majority of patients. A physician may then position speculum 22 whereby the particular region of the cervix to be operated upon extends within notch 58, while shielding surrounding tissues with distal end 26 of speculum body 24, thereby minimizing the likelihood that other tissues will be contacted by electrocautery electrodes or other surgical tools. Preferably, notched opening 58 extends over an angular rotation of approximately 25% (i.e., approximately 90 angular degrees) of the total circumference of open distal end 26 of speculum body 24.

Figure 7:
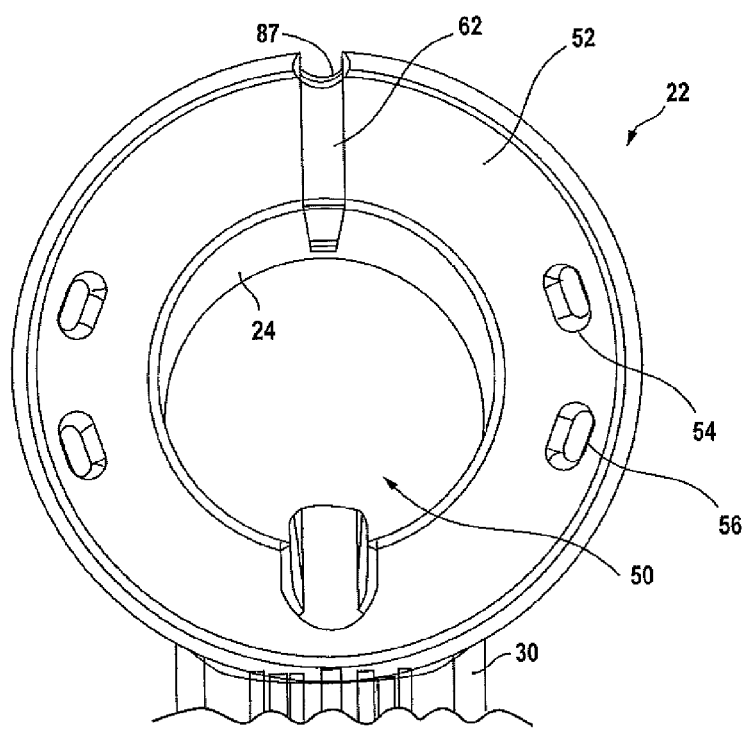
FIG. 7 is a rear view of the speculum without the smoke evacuation insert looking through the cylindrical body thereof.

Referring briefly to FIG. 7, smoke evacuation channel recess 62 is formed in the upper, interior wall of speculum body 24 and truncated cone 52. As viewed in FIG. 7, i.e., before the addition of the aforementioned smoke evacuation insert, smoke evacuation channel recess 62 resembles a slot, integral with speculum body 24 and truncated cone 52, but lacking a bottom wall, and also lacking an end wall to seal smoke evacuation channel recess 62 at its proximal end.

Turning to FIG. 8, a smoke evacuation insert 72 extends between a proximal end 74 and a distal end 76. Located at distal end 76 are two outwardly facing flanges, 77 and 79. Flanges 77 and 79 are designed to increase the cross-sectional area into which smoke or other noxious fumes can flow during procedures. A first channel section 81 is connected to flanges 77 and 79 at a first end thereof. Channel section 81 is designed to attach directly below the slotted smoke evacuation channel recess 62 within speculum body 24 (see FIG. 7). A second channel section 83 mates to channel section 81 at bend region 85 and forms an angle identical to the angle formed by speculum body 24 and truncated cone 52. Channel section 83 is designed to attach directly below the section of smoke evacuation channel recess 62 that resides in truncated cone 52. Extending upwardly from proximal end 74 of smoke evacuation insert 72 is vacuum port connector 60. Vacuum port connector 60 surrounds opening 61; during surgical procedures, a vacuum hose (not shown) is coupled with vacuum port 60 to draw off smoke or other noxious fumes. Any such smoke or fumes are suctioned through flanges 77 and 79 at the distal end of smoke evacuation insert 72, through channel 81, then through channel 83, and finally through opening 61 of port connector 60 at proximal end 74 of smoke evacuation insert 72 into the vacuum hose for safe disposal.

Still referring to FIG. 8, during assembly, smoke evacuation insert 72 is inserted into speculum body 24, and attached using a cement or adhesive such that channel sections 81 and 83 are aligned with smoke evacuation channel recess 62 (see FIG. 7) in speculum body 24 and truncated cone 52, respectively. The bottom portion of vacuum port connector 60 is aligned within notch 87 at the proximal end of truncated cone 52 (see FIG. 7).

Referring to FIG. 5, after assembly of the smoke evacuator insert as previously discussed, smoke evacuation channel 63 is formed by smoke evacuation channel recess 62 in speculum body 24 and truncated cone 52, and channels 81 and 83 of smoke evacuation insert 72. Port 60 extends upwardly from the top of speculum body 24 at approximately proximal end 28. Smoke evacuation port 60 has an aperture 61 extending therethrough and communicating with a smoke evacuation channel 63, formed within passageway 50 of speculum body 24, to evacuate smoke and/or noxious gases generated at the surgical site near distal end 26 of speculum 22. Smoke evacuation channel 63 extends along hollow passageway 50 of speculum body 24, and extends generally from approximately notched opening 58 near the distal end 26 of speculum body 24 toward the proximal end 28 thereof. As shown best in FIG. 5, evacuation port 60 extends outwardly from the exterior wall of conical portion 52 of speculum body 24, allowing a standard vacuum hose to be conveniently coupled thereto without obstructing a physician's view along central passageway 50 of speculum body 24.

Speculum body 24 is preferably formed as an integrally-molded plastic structure from medical-grade plastic using an injection molding process. Preferably, such medical-grade plastic is polycarbonate, which is known as a strong, tough material which is easily molded, which can be optically transparent, and which can resist relatively high temperatures. The term "LEEP" stands for "loop electrosurgical excision procedure", wherein a thin, electrified wire loop is used by a surgeon to cut out abnormal tissue. In order to facilitate the manufacture of speculum 22, smoke evacuation port 60 and channel 62 are preferably formed as a subassembly, and assembled into speculum body 24 in a manner now to be described in conjunction with FIGS. 7-10.

Figure 6:
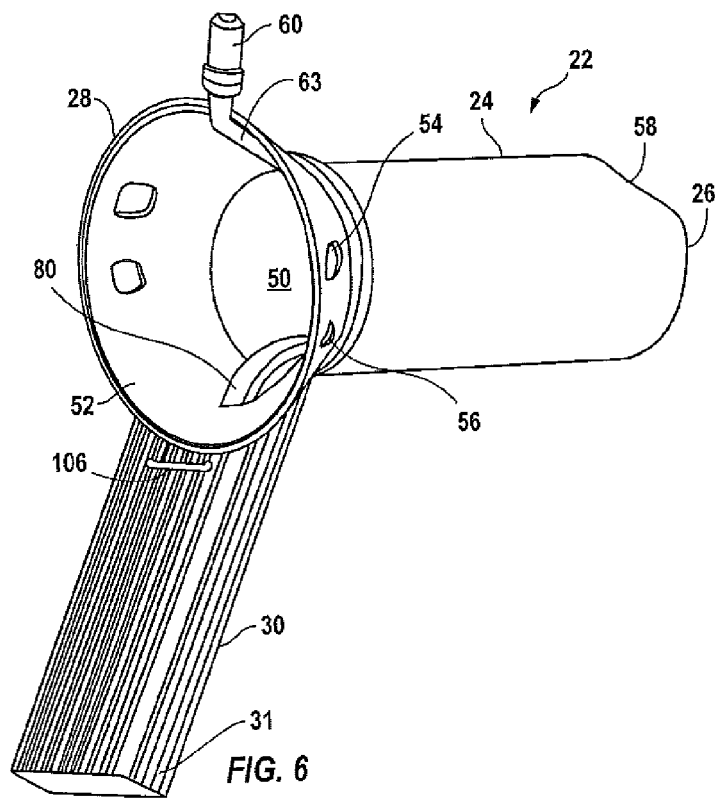
FIG. 6 is a perspective view of the speculum body including the smoke evacuation insert, showing a light guide which extends from the upper portion of the handle through the cylindrical body of the speculum, and the slot for insertion of the color filter.

Referring now to FIGS. 5-7, speculum body 24 also includes a light guide, or light channel, 80. Light guide 80 extends between first and second opposing ends generally along the lower portion of the wall that surrounds the hollow passageway 50 of speculum body 24. As shown best in FIG. 5, the first end 82 of light guide 80 extends within the upper portion of handle 30 for receiving light from a light source. Light guide 80 then makes a bend through approximately a seventy five degree smooth curve and extends to second distal end 84. Light conducted by light guide 80 is emitted at distal end 84 for illuminating the vaginal area being investigated and/or operated upon. Light guide 80 is preferably integrally molded with speculum body 24. To facilitate such transmission of light through light guide 80, the medical-grade plastic used to form speculum body 24, including light guide 80, is preferably clear. Light guide 80 projects partially into hollow passageway 50 of speculum body 24. It will be recalled that obturator 32 includes, along the lower portion thereof, an elongated recessed area 48 (see FIG. 2) which permits obturator 32 to slide past light guide 80, provided that obturator 32 is properly aligned with speculum body 24 during insertion. In this respect, light guide 80 also serves as an alignment channel, allowing obturator 32 to freely move longitudinally within speculum body 24, but resisting angular rotation of obturator 32 relative to speculum body 24.

FIGS. 9 and 10 generally illustrate how obturator 32 snugly fits just below and behind the smoke evacuation insert 72 when fully-inserted into speculum 22. Similarly, FIG. 10 illustrates how recess 48, formed in the bottom of obturator 32, fits over light guide 80, allowing axial movement therebetween, but not rotational movement. When obturator 32 is fully-inserted within speculum 22, the forward edge of upper-projecting tab 42 of planar member 38 lightly engages proximal end 74 of smoke evacuation insert 72

Figure 12:
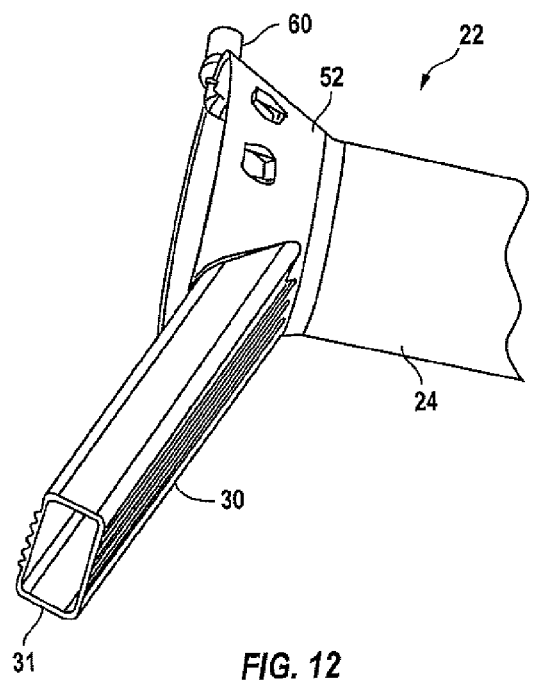
FIG. 12 is a bottom partial perspective view of the handle portion of the speculum and smoke evacuation insert.
Figure 13:
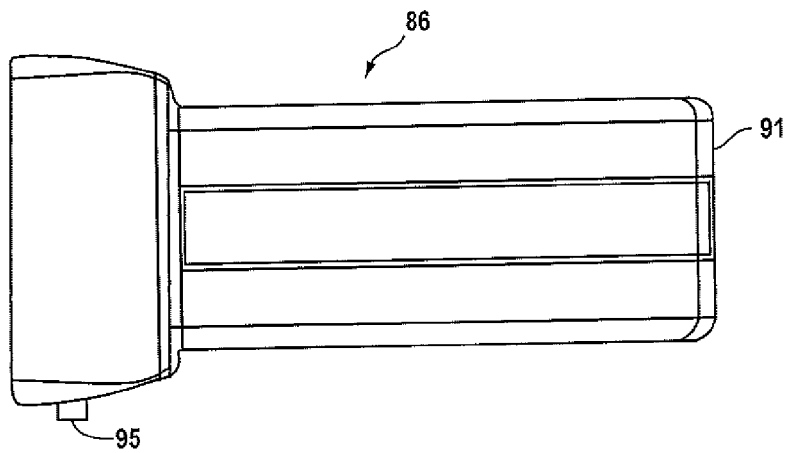
FIG. 13 is a front view of the light source shown in FIG. 1.
Figure 14:
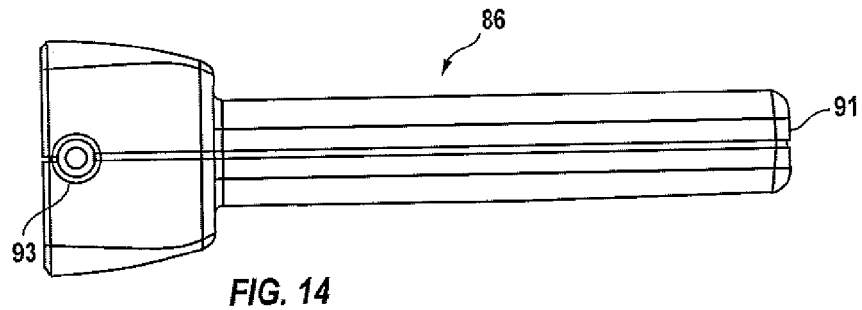
FIG. 14 is a side view of the light source shown in FIGS. 1 and 13.
Figure 15:
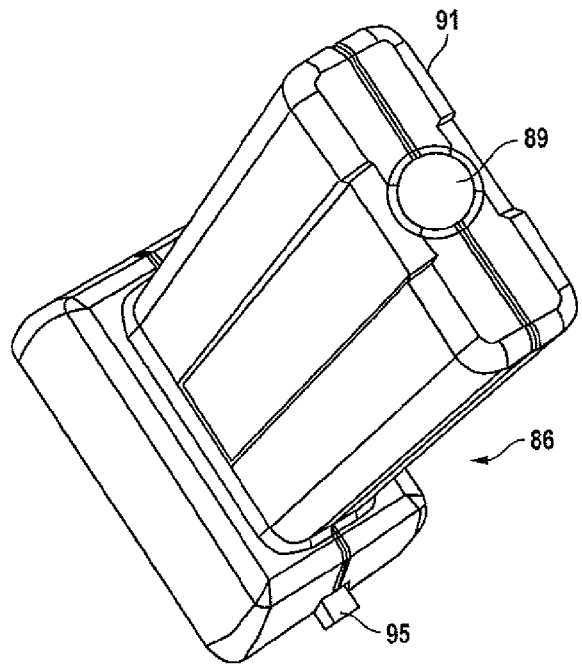
FIG. 15 is a perspective view of the upper portion of the light source shown in FIGS. 1, 13, and 14 and showing the location from which the light is emitted.

As shown in FIGS. 11 and 12, the bottom 31 of handle portion 30 is open. Handle 30 is generally hollow in order to releasably receive and store an elongated light source 86, best shown in FIGS. 13-15. The upper end 91 of light source 86 includes a light emitting diode assembly including lens 89. When light source 86 is fully-inserted into handle 30, lens 89 of the light emitting diode assembly is aligned with first end 82 of light guide 80 for directing light into light guide 80. As shown in FIG. 14, light source 86 preferably includes an electrical jack 93 that may be used to recharge a battery (not shown) within light source 86. In addition, spring-actuated depression switch 95 can be alternately depressed to turn light source 86 on and off, if desired.

Turning to FIGS. 16A and 16B, a color filter assembly 98 is shown in FIG. 16B and consists of a handle flange 102 and a filter tray 105 supporting semi-transparent color filter 107. Filter tray 105 is surrounded on either side by enlarged shoulder regions 101 and 103. Filter tray 105, and its shoulder regions 101 and 103, are designed to fit releasably into slot 106 formed in the upper portion of handle 30, shown best in FIG. 16A. It should be appreciated that, while slot 106 is shown in FIG. 16A as facing toward the proximal end of the speculum (i.e., away from the patient), slot 106 could also be formed in one of the other walls of handle 30. When color filter assembly 98 is inserted into slot 106 as shown in FIG. 17, color filter 107 in filter tray 105 is designed to align with the lens 89 of the light emitting diode assembly of light source 86, as well as with first end 82 of light guide 80. Accordingly, when color filter assembly 98 is inserted into slot 106, the light from light source 86 is directed through the semi-transparent color filter 107 to create a desired color of light. Semi-transparent color filter 107 is preferably constructed of polycarbonate, and is 3 to 5 mils (0.003"-0.005") in thickness, such as the Roscolux line of color filters offered by Rosco Laboratories of Stamford Conn. Any number of such color filter assemblies 98 may be kept on hand, each of a unique color, to best accentuate the particular tissues under study; one such color filter may be removed, and another inserted in its place, in a relatively quick and easy manner. On the other hand, if broad spectrum white light is desired, color filter assembly 98 is simply removed.

In another preferred embodiment shown in FIGS. 18 and 19, color filter assembly 201 consists of a circular insert 202 and semi-transparent color filter 203. Assembly 201 is designed such that at least a first portion 210 of its total area is fully transparent to light, and at least a second portion of its total area is covered with a semi-transparent filter 203. Filter assembly 201 may also feature cylindrical pivot posts 204 and 205, best seen in FIG. 19, extending upwardly and downwardly to aid in the support and rotation of filter assembly 201. In the embodiment shown in FIGS. 18 and 19, filter assembly 201 is shown with equal areas of transparent (210) and semi-transparent (203) material; however it should be obvious to those skilled in the art that additional areas may be produced to feature semi-transparent films of different color spectra. For example, FIG. 29 illustrates a three-position filter assembly 201' having a circular outer frame 202' coupled with pivot post 204', a first color filter 203' of a first color, a second color filter 206' of a second color, and transparent region 210".

To facilitate the use of color filter assembly 201, receiving tabs 206, 207, 208 and 209 may be added to handle 30 of speculum 22 as shown in FIG. 22. Receiving tabs 206 and 207 extend above slot 106 and rotatably support pivot post 204 with a snap fit; receiving tabs 208 and 209 extend below slot 106 and rotatably support pivot post 205 with a snap fit. Filter assembly 201 may be assembled to handle 30 by inserting the assembly 201 into slot 106 within handle 30, and by further inserting pivot post 204 into receiving tabs 206 and 207, and by inserting pivot post 205 into receiving tabs 208 and 209. Thereafter, color filter assembly 201 may be rotated about pivot posts 204 and 205 by the user. In FIG. 20, color filter assembly 201 is shown rotated to the position wherein the transparent portion 210 thereof lies between lens 89 of light source 86 and first end 82 of light guide 80. In FIG. 21, color filter assembly 201 has been rotated 180 degrees to place the semi-transparent color filter 203 between lens 89 of light source 86 and first end 82 of light guide 80.

Once again, while FIGS. 20-22 indicate that slot 106 is formed facing toward the proximal end of the speculum (i.e., away from the patient), slot 106 could also be formed in one of the other walls of handle 30. In addition, those skilled in the art will appreciate that color filter wheel 201 of FIGS. 18-21, and color filter wheel 201' of FIG. 29, may be permanently housed within handle 30; in this case, only a portion of the perimeter of circular frame 202/202' protrudes through the exterior of handle 30 through slot 106 for allowing the user to move the color wheel with the user's thumb, or forefinger, depending on the location of slot 106 within handle 30.

Those skilled in the art will appreciate that, while FIGS. 18-22 and 29 illustrate embodiments in which one or more color filters are configured as a rotatable wheel, various other configurations may be used whereby one or more color filters are rotated, pivoted, or otherwise moved, into and out of the path of light between the output of the light source and the first end of the light channel.

Figure 26A:
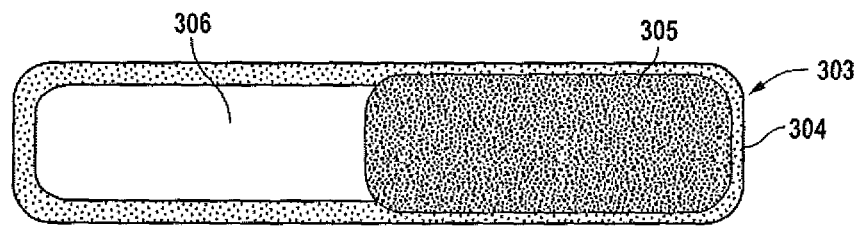
FIG. 26A is a top view of an elongated rectangular color filter insert for use with the speculum handle shown in FIGS. 23-25.
Figure 26B:
FIG. 26B is a side view of the color filter insert shown in FIG. 26A.
Figure 27:
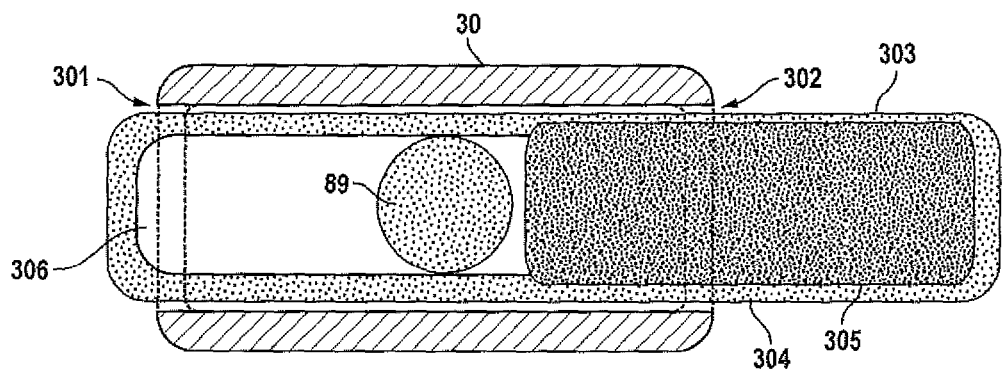
FIG. 27 is a top sectional view of the speculum handle, similar to FIG. 25, and showing a first position of the insert shown in FIGS. 26A and 26B.
Figure 28:
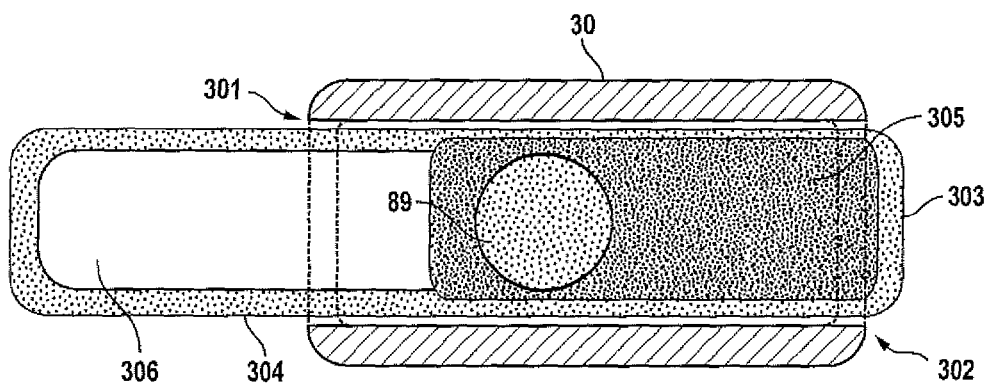
FIG. 28 is a top sectional view of the speculum handle, similar to FIG. 27, and showing a second position of the insert shown in FIGS. 26A and 26B.

Yet another preferred embodiment will now be described in conjunction with FIGS. 23-28. Slots 301 and 302 are cut into the sides of handle 30, as best seen in FIGS. 23-25, just above the point at which lens 89 of light source 86 is situated. As shown in FIGS. 26A and 26B, a color filter slider 303 consists of a rectangular plastic frame 304, a portion of which is covered with semi-transparent color film 305. The open portion 306 of frame 304 remains fully transparent to light. In the embodiment shown in FIGS. 26A and 26B, filter assembly 303 is shown with transparent portion 306 and semi-transparent color filter portion 305 being of equal area; however it should be obvious to those skilled in the art that additional areas may be produced to feature semi-transparent films of different color spectra. The length of filter assembly 303 is greater than the width of handle 30, for reasons which will become apparent. Filter assembly 303 is inserted into handle 30 by sliding it into slot 301 and partially outward through opposing slot 302, or vice-versa. Because the length of filter assembly 303 is greater than the width of handle 30, either the transparent portion 306 or the semi-transparent color filter 305 may be placed in line with lens 89 of light source 86 and first end 82 of light guide 80. Referring to FIG. 27, color filter slider 303 has been moved to the position wherein transparent material 306 lies between lens 89 and light guide 80. On the other hand, in FIG. 28, color filter slider 303 has been moved to the position wherein semi-transparent color filter portion 305 lies between lens 89 and light guide 80. In this fashion, by sliding color filter assembly 303 through slots 301 and 302, the user may select whether the light from light source 86 passes through fully-transparent portion 306 or semi-transparent, color-filtered portion 305. A number of such color filter sliders may be provided, if desired, each having a unique color filter frequency, for allowing the user to select the best color to highlight the tissues being examined.

Those skilled in the art will now appreciate that a new and improved speculum has been disclosed that improves visualization for the physician, increases comfort for the patient, and decreases the risk of injury to the patient. The light guide incorporated into the speculum body, and light source received within the speculum handle, allow for optimal visualization of the operative site without the need for a gooseneck light or other light source. The light source may be a currently available battery-powered, portable, broad spectrum, white light source, and the light may be selectively filtered to provide for illumination by different colors across the color spectrum. The novel light filtering capability is designed to view abnormal epithelium such as blood vessel punctation, acetowhite change and abnormal Lugol's iodine staining which would allow more exact excision of abnormal epithelium for diagnostic and treatment purposes. Moreover, by providing a simple and easy method for inserting and removing color filters of specific desired color frequencies, one avoids the need to generate such colors by mixing primary colors together.

Because the new speculum is generally cylindrical, a physician can more completely visualize the cervix or other area being investigated. In addition, since the inner passageway of the speculum is completely enclosed, the sidewalls of the orifice are prevented from encroaching on the operative field. Apart from maintaining an improved field of view, exclusion of the sidewalls from the inner passage of the speculum reduces the risk of injury to surrounding epithelium during application of electrical current, even if the patient makes an inadvertent movement. In addition, the formation of a notched opening at the distal end of the speculum body allows the user to position the speculum so that the area of interest drops into the speculum. Moreover, the use of the obturator in combination with the speculum during initial placement facilitates insertion of the speculum into the vagina or other orifice with minimal discomfort to the patient.

The conical shaped opening at the proximal end of the speculum provides easy access to the operative site, as well as a large working area for the surgeon. The oval-shaped fenestrations provided on the conical-shaped proximal end of the speculum allow the speculum to be easily sutured to the labia, or other surrounding outer tissues, in order to secure it into the vagina during surgical procedures if so desired.

The smoke evacuation channel, and laterally-extending smoke evacuation port, allow for convenient evacuation of effluvium which can be toxic and obscure the operative field of vision. The smoke evacuation port may be attached to standard suction tubing, which is maintained away from the user's line of sight. The manufacture of a separate smoke evacuation channel, and the method of securing the smoke evacuation channel inside the speculum body, provide for a relatively inexpensive technique for achieving evacuation of smoke and noxious gases.

While the present invention has been described with respect to preferred embodiments thereof, such description is for illustrative purposes only, and is not to be construed as limiting the scope of the invention. Various modifications and changes may be made to the described embodiments by those skilled in the art without departing from the true spirit and scope of the invention as defined by the appended claims.

We claim:

1. A speculum comprising in combination:
   a. a generally cylindrical body, the generally cylindrical body including an open distal end for insertion into a body cavity and an opposing open proximal end through which an internal tissue area may be examined, the generally cylindrical body having a generally cylindrical hollow passageway extending therethrough;
   b. a handle coupled to the proximal end of the generally cylindrical body, the handle extending generally laterally from the generally cylindrical body;
   c. a light source receivable within the handle for providing broad spectrum white light;
   d. a light channel which extends along the generally cylindrical body to direct light from the light source toward the distal end of the generally cylindrical body in order to illuminate the body cavity;
   e. a first color filter selectively insertable within a space located between the light source and the light channel to selectively illuminate the body cavity with light of a first color spectrum.

2. The speculum recited by claim 1 wherein the first color filter is selectively removable from the space located between the light source and the light channel to illuminate the body cavity with unfiltered broad spectrum white light.

3. The speculum recited by claim 1 wherein the space located between the light source and the light channel is a slot formed in the handle, and wherein the first color filter may be inserted into and removed from the slot formed in the handle, thereby changing the spectrum of light illuminating the body cavity.

4. The speculum recited by claim 3 including a second color filter adapted to be inserted into, and removed from, the slot formed in the handle, the second color filter being of a different color than the first color filter.

5. The speculum recited by claim 1 wherein the first color filter is rotatably supported within the handle and may be selectively rotated into the space located between the light source and the light channel to illuminate the body cavity with light of a first color spectrum.

6. The speculum recited by claim 5 wherein the first color filter may be selectively rotated out of the space located between the light source and the light channel to illuminate the body cavity with unfiltered broad spectrum white light.

7. The speculum recited by claim 1 wherein the first color filter is 0.003" to 0.005" thick.

8. The speculum recited by claim 1 wherein the first color filter is selected to illuminate the body cavity with blue-green light.

9. The speculum recited by claim 5 including a color wheel rotatably supported within the handle, the first color filter being included in the color wheel, and the color wheel including a second color filter spaced from the first color filter, the second color filter being of a different color than the first color filter, wherein the color wheel is adapted to be rotated to selectively position one of the first and second color filters into the space located between the light source and the light channel to illuminate the body cavity with light of a corresponding color spectrum.

10. The speculum recited by claim 1 wherein the first color filter is secured to a slider assembly slidingly supported within the handle, wherein a user can slide the slider assembly to a first position for inserting the first color filter within the space located between the light source and the light channel, and wherein the user can slide the slider assembly to a second position wherein the first color filter is removed from the space located between the light source and the light channel, to alter the spectrum of light illuminating the body cavity.

11. The speculum recited by claim 10 wherein unfiltered broad spectrum white light passes from the light source to the light channel when the slider assembly is at its second position.

12. A gynecological speculum comprising in combination:
 a. a generally cylindrical body, the generally cylindrical body including an open distal end for insertion into a vaginal area and an opposing open proximal end through which the vaginal area may be examined, the generally cylindrical body having a generally cylindrical hollow passageway extending therethrough;
 b. a handle coupled to the proximal end of the generally cylindrical body, the handle extending generally laterally from the generally cylindrical body;
 c. a light source receivable within the handle for providing broad spectrum white light;
 d. a light channel which extends along the generally cylindrical body to direct light from the light source toward the distal end of the generally cylindrical body in order to illuminate the vaginal area;
 e. a first color filter selectively insertable within a space located between the light source and the light channel in order to selectively illuminate the vaginal area with light of a first color spectrum.

13. The gynecological speculum recited by claim 12 wherein the first color filter is selectively removable from the space located between the light source and the light channel to illuminate the vaginal area with unfiltered broad spectrum white light.

14. The gynecological speculum recited by claim 12 wherein the space located between the light source and the light channel is a slot formed in the handle, and wherein the first color filter may be inserted into and removed from the slot formed in the handle, thereby changing the spectrum of light illuminating the vaginal area.

15. The gynecological speculum recited by claim 14 including a second color filter adapted to be inserted into, and removed from, the slot formed in the handle, the second color filter being of a different color than the first color filter.

16. The gynecological speculum recited by claim 12 wherein the open distal end of the generally cylindrical body includes a notched opening for allowing a cervical portion of a patient to enter into the generally cylindrical hollow passageway of the generally cylindrical body.

17. The gynecological speculum recited by claim 12 wherein the truncated conical portion formed at the open proximal end of the generally cylindrical body has a plurality of apertures formed therein to allow sutures to be passed through said plurality of apertures for suturing the truncated conical portion to a patient's body.

18. The gynecological speculum recited by claim 12 wherein the first color filter is rotatably supported within the handle and may be selectively rotated into the space located between the light source and the light channel to illuminate the vaginal area with light of a first color spectrum.

19. The gynecological speculum recited by claim 18 wherein the first color filter may be selectively rotated out of the space located between the light source and the light channel to illuminate the vaginal area with unfiltered broad spectrum white light.

20. The speculum recited by claim 12 wherein the first color filter is 0.003" to 0.005" thick.

21. The speculum recited by claim 12 wherein the first color filter is selected to illuminate the body cavity with blue-green light.

22. The gynecological speculum recited by claim 12 including a color wheel rotatably supported within the handle, the first color filter being included in the color wheel, and the color wheel including a second color filter spaced from the first color filter, the second color filter being of a different color than the first color filter, wherein the color wheel is adapted to be rotated to selectively position one of the first and second color filters into the space located between the light source and the light channel to illuminate the vaginal area with light of a corresponding color spectrum.

23. The gynecological speculum recited by claim 12 wherein the first color filter is secured to a slider assembly slidingly supported within the handle, wherein a user can slide the slider assembly to a first position for inserting the first color filter within the space located between the light source and the light channel, and wherein the user can slide the slider assembly to a second position wherein the first color filter is removed from the space located between the light source and the light channel, to alter the spectrum of light illuminating the vaginal area.

24. The gynecological speculum recited by claim 23 wherein unfiltered broad spectrum white light passes from the light source to the light channel when the slider assembly is at its second position.

* * * * *